(12) United States Patent
Castro (10) Patent No.: US 11,980,552 B2
(45) Date of Patent: May 14, 2024

(54) BIOCOMPATIBLE CONSTRUCTION FOR IMPLANTATION INTO A JOINT

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 300 days.

(21) Appl. No.: 17/681,780

(22) Filed: Feb. 27, 2022

(65) Prior Publication Data

US 2022/0175551 A1 Jun. 9, 2022

Related U.S. Application Data

(63) Continuation-in-part of application No. PCT/US2020/054166, filed on Oct. 3, 2020.

(51) Int. Cl.
*A61F 2/46* (2006.01)
*A61B 17/16* (2006.01)
*A61F 2/44* (2006.01)

(52) U.S. Cl.
CPC ........ *A61F 2/4644* (2013.01); *A61B 17/1671* (2013.01); *A61F 2/4405* (2013.01); *A61F 2/4455* (2013.01); *A61F 2/447* (2013.01); *A61F 2/4611* (2013.01); *A61F 2002/4627* (2013.01); *A61F 2002/4649* (2013.01)

(58) Field of Classification Search
CPC ... A61B 17/02; A61B 17/0206; A61B 17/025; A61B 17/86; A61B 17/88; A61B 17/68; A61F 2/44; A61F 2/442; A61F 2/447; A61F 2/46
See application file for complete search history.

(56) References Cited

U.S. PATENT DOCUMENTS

| | | | |
|---|---|---|---|
| 6,770,096 B2 | 8/2004 | Bolger et al. | |
| 8,366,774 B1 | 2/2013 | Bruffey et al. | |
| 9,421,112 B2 | 8/2016 | Bal et al. | |
| 2009/0054988 A1 | 2/2009 | Hess | |
| 2011/0054530 A1 | 3/2011 | Lins | |
| 2014/0088715 A1 | 3/2014 | Ciupik | |
| 2014/0094918 A1 | 4/2014 | Vishnubholta et al. | |
| 2019/0131417 A1 | 10/2019 | Castro | |

*Primary Examiner* — Christopher J Beccia
(74) *Attorney, Agent, or Firm* — BUSINESS PATENT LAW, PLLC (57) ABSTRACT

A biocompatible construction adapted for use in joint surgeries. Among other things, the joint implant has an anterior cutting edge and a rotatable cutter distinct from the cutting edge. The rotatable cutter allows for graduated cutting of biological tissue or structure.

20 Claims, 10 Drawing Sheets

BIOCOMPATIBLE CONSTRUCTION FOR IMPLANTATION INTO A JOINT

PRIORITY

Applicant claims priority to PCT/US2020/054166—Biocompatible Construction for Implantation into a Joint—filed on Oct. 3, 2020 that claims the benefit of U.S. Provisional Application No. 62/975,244—Biocompatible Construction for Implantation into a Joint—filed on Feb. 12, 2020.

BACKGROUND OF THE INVENTION

A. Field of the Invention

The present invention is an implant for a joint or a surgically created cavity. Among other things, the biocompatible construction for implantation into a joint or surgically created cavity has an anterior cutting edge as well as a rotatable cutter. Preferred embodiments of the biocompatible construction include a rotatable cutter with windows disposed between first and second sections of the rotatable cutter. Select preferred embodiments of the rotatable cutter can be provided with sections that are curvilinear through multiple planes. Among other things, prior to the current invention, it is believed there were no available implants for implantation into a joint or surgically created cavity where the implants had teeth capable of generating an autograft of subchondral bone in a joint space or surgically created cavity.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art include: 1) U.S. Pat. No. 6,770,096—Bolger, et al. that discloses an interbody spinal stabilization cage and spinal stabilization method; 2) U.S. Pat. No. 8,366,774—Bruffey, et al. discloses a spinal cage having deployable member; 3) US Published Patent Application No. 20140094918—Vishnubholta, et al. discloses a stand-alone interbody fixation system; 4) U.S. Pat. No. 9,421,112-Bal, et al. discloses a fixation system for spinal cages; 5) US Published Patent Application No. 20110054530—Lins discloses a surgical implant device for the translation and fusion of a facet joint of the spine; 6) US Published Patent Application 201901314171 discloses a joint implant; 7) US Published Patent Application 20090054988—Hess discloses interspinous implants and methods for implanting same; and 8) US Published Patent Application 20140088715—Ciupik discloses an intervertebral implant for mutual situating of adjacent vertebrae.

Among other things, none of the above listed references disclose a biocompatible construction (100) for implantation into a joint or surgically created cavity; the biocompatible construction (100) comprising: a) a single-piece frame (240) comprising: i) a surgeon facing side (200) comprising a bearing (210); ii) a first lateral bend (260) extending away from a plane of the surgeon facing side (200); iii) a second lateral bend (270) extending away from the plane of the surgeon facing side (200); b) a complimentary anterior plate (750) adapted to distract and to cut with application of forward force; the complimentary anterior plate (750) connected to: i) an exposed end (264) of first lateral bend (260) of the single-piece frame (240); ii) an exposed end (274) of second lateral bend (270) of the single-piece frame (240); and c) a rotatable single-piece cutter (600) having a longitudinal axis (X-X), a height axis (Y-Y) and a depth axis (Z-Z); the rotatable single-piece cutter (600) connected to the bearing (210) and the inward side (752) of the anterior plate (750); the rotatable single-piece cutter (600) comprising: a first plurality of first teeth (632) positioned outward from the longitudinal axis (X-X) and a second plurality of second teeth (652) positioned outward from the longitudinal axis (X-X); the first plurality of first teeth (632) and the second plurality of second teeth (652) adapted to generate an autograft having particle sizes in the range of from about 50 cubic millimeters to about 6 cubic millimeters or less.

SUMMARY OF THE INVENTION

The more tools or instruments inserted into a surgical field, the greater the possibility of an error resulting in patient injury. Due to the simplicity of the current biocompatible construction, a number of surgical tools required and steps associated with performing prior state-of-the-art fusions can be eliminated. Among other things, use of the current invention allows arthrodesis procedures to be performed in the cervical spine, sacroiliac joint, ankle, hand or other similar joints.

One of the currently available state-of-the art techniques for cervical fusions is the DTRAX system. The DTRAX spinal system uses five instruments, a working cannula, and numerous steps. A working cannula with a chisel is used to breach the desired posterior facet joint. Once in position, the chisel is removed and a broach is inserted through the working cannula. The broach is advanced and retracted several times in order to remove the cartilaginous end-plates. After the broach is removed from the working cannula, a drill is inserted. After drilling is completed, a second rasp is placed to decorticate the posterior cortex. After the use of the second rasp is completed, the fixation device (filled with graft material) is inserted through the working cannula into the joint. Additional graft material is then impacted behind the implant.

Current state-of-the-art sacroiliac surgical procedures require a fusion device that is either inserted from a posterior or lateral approach. Applicant's understanding is: there are fusion devices for use with either the posterior approach or the lateral approach, but the same fusion device is incapable for use with both the posterior and the lateral approaches. Many of the current sacroiliac fusion procedures require the use of working cannulas, numerous broaches, rasps, drills and other devices that tend to complicate the surgical procedure. Applicant's current biocompatible construction can accomplish sacroiliac fusions through either a posterior or lateral approach with fewer surgical tools and steps.

Unlike other joint implants, among other things, the present biocompatible construction can include a rotatable cutter with first and second sections that are curvilinear through multiple planes. Such structures can provide for graduated cutting of structures such as bone and other tissues. Preferred embodiments of the cutter include a stub axle, connector and windows.

An aspect of the present invention is to provide a biocompatible construction with an anterior side having a cutting edge.

Still another aspect of the present invention is to provide a biocompatible construction with an anterior side including a socket.

It is yet another aspect of the present invention to provide a cutter with one or more openings, windows and apertures.

Still another aspect of the present invention is to provide a cutter with a stub axle at one end of the biocompatible construction and a connector at the opposite end of the biocompatible construction.

It is still another aspect of the present invention to provide first and second sections, where relative to the biocompatible construction's longitudinal axis, each section includes a first curvature that curves from a first point more proximate the longitudinal axis toward a second point more distance from the longitudinal axis.

Yet still another aspect of the present invention is to provide a biocompatible construction where rotation of the rotatable cutter causes the first or the second section or both to extend beyond the biocompatible construction.

Still another aspect of the present invention is to provide sections of the rotatable cutter with blades to cut the biological structure or tissue and opposed noncutting edges.

It is still another aspect of the present invention to provide the section's blade with a concave bend relative to the noncutting edge.

Yet another aspect of the present invention is to provide a biocompatible construction that, after insertion into the surgically created opening, provides distraction.

It is yet another aspect of the present invention is to provide a biocompatible construction where, after insertion into the posterior cervical facet joint, the distraction can indirectly provide some neuroforaminal decompression.

It is still another aspect of the present invention to provide a biocompatible construction that can lessen any biocompatible construction subsidence.

Yet still another aspect of the present invention is to provide a biocompatible construction that includes surface treatments. Surface treatments can improve fixation of the biocompatible construction, and it is believed that when the biocompatible construction is inserted at an angle perpendicular to the joint surfaces, surface treatments significantly improve fusion.

Still another aspect of the present invention is to provide a biocompatible construction with an anterior side including a receptacle.

Yet another aspect of the present invention is to provide a biocompatible construction with a single-piece frame and an attached complimentary plate including an uninterrupted exterior face.

It is yet another aspect of the present invention is to provide a biocompatible construction including one or more welds to attach the complimentary plate to the single-piece frame.

It is still another aspect of the present invention to provide a biocompatible construction with a lock for locking the rotatable cutter at preselected position.

Yet still another aspect of the present invention is to provide a biocompatible construction including a rotatable cutter for generating a local autograph of subchondral bone at the joint or surgically created cavity.

Still another aspect of the present invention is to provide a biocompatible construction with a rotatable cutter with a centralized aperture adapted to enhance dispersal of the generated autograft about the joint or surgically created cavity.

Yet another aspect of the present invention is to provide a biocompatible construction with first and second teeth positioned on the rotatable cutter at locations where some of the first teeth are three dimensionally diverse to other first teeth and some of the second teeth are three dimensionally diverse to other second teeth.

It is still another aspect of the present invention to provide peripheral edges of the rotatable cutter that create lengthwise tracks for the first and second teeth of the rotatable cutter where the lengthwise tracks cause some of the first teeth to be positioned in at least one of the three axes (X-X, Y-Y, Z-Z) distinct from the positions and locations of other first teeth and some of the second teeth to be positioned in at least one of the three axes (X-X, Y-Y, Z-Z) distinct from the positions and locations of other second teeth.

A preferred embodiment of the current invention can be described as a biocompatible construction for implantation into a joint or surgically created cavity; the biocompatible construction comprising: a) a frame comprising: i) a surgeon facing side comprising a bearing; ii) a first side of a first lateral support connected to a first side of the surgeon facing side and a second side of the first lateral support opposite from the surgeon facing side; and iii) a first side of a second lateral support connected to a second side of the surgeon facing side, opposite from the first side of the first lateral support, and a second side of the second lateral support opposite from the surgeon facing side; b) a rotatable integral cutter adapted to generate an autograft of articular cartilage and subchondral bone at the joint or surgically created cavity; the rotatable integral cutter further comprising: i) a central body comprising; a longitudinal axis (X-X), a height axis (Y-Y) and a depth axis (Z-Z) extending through the rotatable integral cutter; a centralized aperture adapted to enhance dispersal of the generated autograft about the joint or surgically created cavity; a first flared section, positioned on a first side of the central body, extending away from the longitudinal axis (X-X); the first flared section comprising first teeth, wherein relative to the longitudinal axis (X-X), the height axis (Y-Y) and depth axis (Z-Z) of the rotatable integral cutter, locations of at least some of the first teeth are three dimensionally diverse from other first teeth; a second flared section, positioned on a second side of the central body, extending away from the longitudinal axis (X-X); the second flared section comprising second teeth, wherein relative to the longitudinal axis (X-X), the height axis (Y-Y) and depth axis (Z-Z) of the rotatable integral cutter, locations of at least some of the second teeth are three dimensionally diverse from other second teeth, and wherein first and second teeth generate the autograft having particle sizes in the range of from about 50 cubic millimeters to about 6 cubic millimeters or less; ii) a first stub axle extending away from the central body, along the longitudinal axis (X-X) and into the bearing; iii) a second stub axle extending away from the central body, along the longitudinal axis (X-X), in a direction opposite the bearing; c) an anterior plate, attached to the frame, adapted to distract and to cut with application of forward force; the anterior plate comprising: i) an interior side comprising a receptacle adapted to engage a nose of the second stub axle; ii) an uninterrupted exterior face comprising an anterior cutting edge, wherein the anterior cutting edge of uninterrupted exterior face is of lesser length than the interior side of uninterrupted exterior face; and iii) first and second blunted zones extending between opposed ends of the anterior cutting edge and external margins of the interior side; d) one or more welds securing the anterior plate to the nose of the second stub axle, the second side of the first lateral support and the second side of the second lateral support; and e) a lock adapted to secure the first flared section and the second flared section in a direction aligned with the height axis (X-X) of the integral rotatable cutter.

Another preferred embodiment of the current invention can be described as a biocompatible construction for implantation into a joint or surgically created cavity; the biocompatible construction comprising: a) an integral frame comprising: i) a surgeon facing side comprising a bearing; ii) a first lateral bend extending away from a plane of the surgeon facing side; iii) a second lateral bend extending away from the plane of the surgeon facing side; b) a rotatable integral cutter adapted to generate an autograft of articular cartilage and subchondral bone at the joint or surgically created cavity; the rotatable integral cutter further comprising: i) a central body comprising; a longitudinal axis (X-X), a height axis (Y-Y) and a depth axis (Z-Z) extending through the rotatable integral cutter; a centralized aperture adapted to enhance dispersal of the generated autograft about the joint or surgically created cavity; a first flared section, positioned on a first side of the central body, extending away from the longitudinal axis (X-X); the first flared section comprising first teeth, wherein relative to the longitudinal axis (X-X), the height axis (Y-Y) and depth axis (Z-Z) of the rotatable integral cutter, locations of at least some of the first teeth are three dimensionally diverse from other first teeth; a second flared section, positioned on a second side of the central body, extending away from the longitudinal axis (X-X); the second flared section comprising second teeth, wherein relative to the longitudinal axis (X-X), the height axis (Y-Y) and depth axis (Z-Z) of the rotatable integral cutter, locations of at least some of the second teeth are three dimensionally diverse from other second teeth, and wherein first and second teeth generate the autograft having particle sizes in the range of from about 50 cubic millimeters to about 6 cubic millimeters or less; ii) a first stub axle extending away from the central body, along the longitudinal axis (X-X) and into the bearing; iii) a second stub axle extending away from the central body, along the longitudinal axis (X-X), in a direction opposite the bearing; c) an anterior plate adapted to distract and to cut with application of forward force; the anterior plate comprising: i) an interior side comprising a receptacle adapted to engage a nose of the second stub axle; and ii) an uninterrupted exterior face comprising an anterior cutting edge, wherein the anterior cutting edge of uninterrupted exterior face is of lesser length than the interior side of uninterrupted exterior face; and d) one or more welds securing the anterior plate to the nose of the second stub axle, the first lateral bend and the second lateral bend.

Still another preferred embodiment of the current invention can be described as a biocompatible construction for implantation into a joint or surgically created cavity; the biocompatible construction comprising: a) a single-piece frame comprising: i) a surgeon facing side comprising a bearing; ii) a first lateral bend extending away from a plane of the surgeon facing side; iii) a second lateral bend extending away from the plane of the surgeon facing side; b) a complimentary anterior plate adapted to distract and to cut with application of forward force; the complimentary anterior plate connected to: i) an exposed end of first lateral bend of the single-piece frame; ii) an exposed end of second lateral bend of the single-piece frame; and c) a rotatable single-piece cutter having a longitudinal axis (X-X), a height axis (Y-Y) and a depth axis (Z-Z); the rotatable single-piece cutter connected to the bearing and the inward side of the anterior plate; the rotatable single-piece cutter comprising: a first plurality of first teeth positioned outward from the longitudinal axis (X-X) and a second plurality of second teeth positioned outward from the longitudinal axis (X-X); the first plurality of first teeth and the second plurality of second teeth adapted to generate an autograft having particle sizes in the range of from about 50 cubic millimeters to about 6 cubic millimeters or less.

It is the novel and unique interaction of these simple elements which creates the current biocompatible construction. Pursuant to the Articles of the Patent Cooperation Treaty and/or Title 35 of the United States Code, select preferred embodiments of the current invention follow. However, it is to be understood that the descriptions of the preferred embodiments do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention. As used herein, with respect to the biocompatible construction (100): 1) "anterior" of the biocompatible construction (100) means the side of the biocompatible construction most distant from the surgeon and 2) "posterior or surgeon-facing side" of the biocompatible construction (100) means the side of the biocompatible construction nearest the surgeon.

In the most general sense, the present invention can result in joint arthrodesis where the biocompatible construction is surgically inserted into or across a joint space or a surgically created cavity. The current biocompatible construction can be useful for surgeries that can assist in stabilizing injured, deformed and or degenerative joints. Preferred embodiments of the current invention can be employed with ankle, cervical, hand, sacroiliac or other orthopaedic procedures. It appears that the present system is particularly useful for posterior cervical fusions and sacroiliac joint fusions. However, the current invention can also be used to fuse the tibia to the talus, the talus to the calcaneus, and metacarpals to the phalanges.

Preferred embodiments of the current biocompatible constructions can be manufactured of titanium alloys, stainless steel, non-resorbable polymers or any other composition acceptable in the art. Meeting a long felt but unfilled need in the orthopaedic surgical arts, the novel and unique structures of the present biocompatible constructions allow the surgical team to, among other things, simplify previous procedures.

The present invention has an anterior side with an anterior cutting edge and a rotatable cutter about the longitudinal axis of the biocompatible construction. In preferred embodiments, lateral openings of the biocompatible construction are outward from the longitudinal axis. The anterior cutting edge of the biocompatible construction is capable of dissecting through adipose, muscle and/or joint capsule tissues. The rotatable cutter of the implant is capable of cutting cartilage and bone and can be associated with the creation of the surgical cavity. Further, the rotatable cutter can morselize bone in preparation for fusion. The combination of the biocompatible construction's anterior cutting edge and blades meet long felt but unfilled needs in the orthopedic surgical arts: among other things, these novel and unique structures allow the surgeon to simplify the previous operating procedures utilized for posterior cervical, sacroiliac, and other joint fusions.

Devices that insert biocompatible, osteogenic and/or other substances into or out of the interior volume of the biocompatible construction can be used with preferred embodiments of the present invention. The current biocompatible construction is also compatible with flexible drills, fiber optics, vacuums, one or more cannulas and one or more devices for inserting the biocompatible construction. Combinations of one or more of the before identified ancillary devices and the current biocompatible construction can assist with the creation and healing of the surgical wound.

Lateral openings of the biocompatible construction as well as the rotatable cutter's windows and apertures can increase the probability of the osteogenic materials and/or arthrodesis accelerating substances procuring a blood supply. And it is believed that increasing the blood supply to the osteogenic materials held by the biocompatible construction increases the probability of successful fusion. Introduction of osteogenic and other substances into the biocompatible construction can hasten the healing of the surgical wound.

Figure 1:
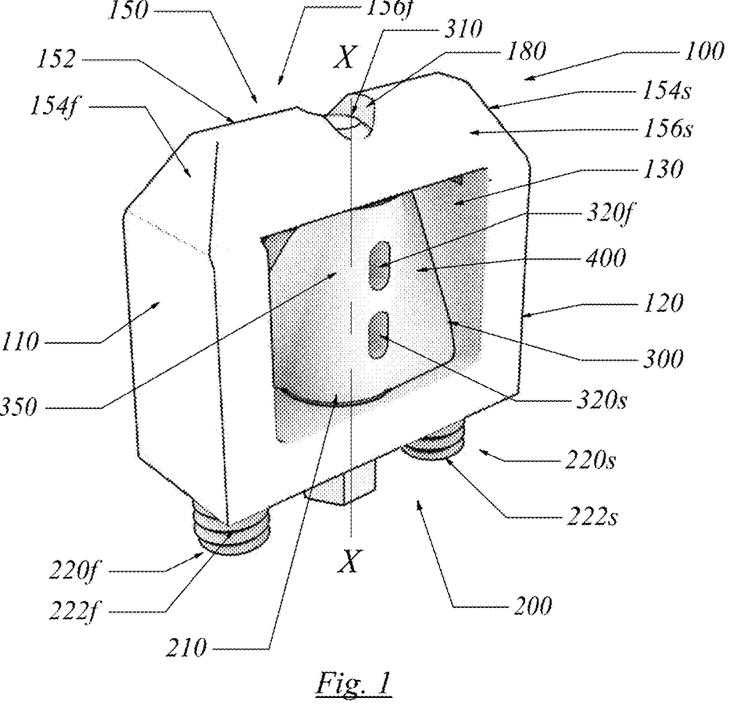
FIG. 1 is a first lateral perspective of a preferred embodiment of biocompatible construction (100).
Figure 2:
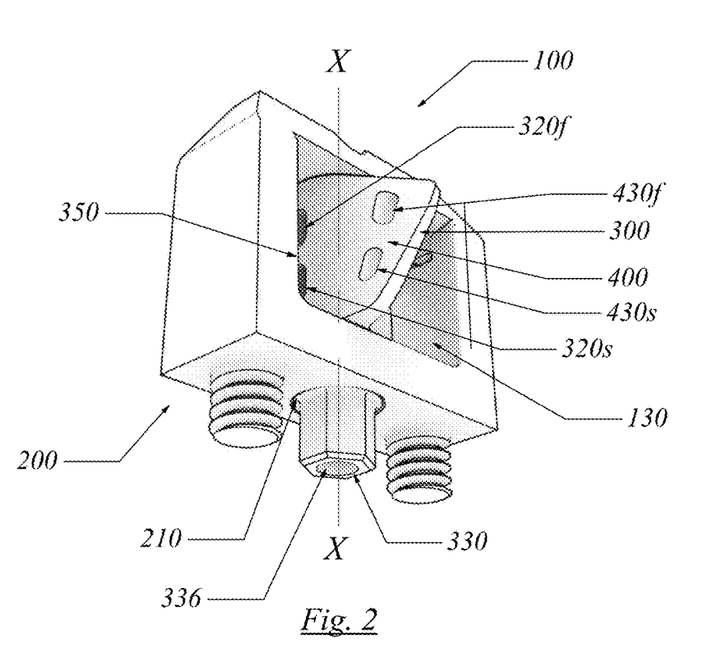
FIG. 2 is a second lateral perspective of the FIG. 1 preferred embodiment of biocompatible construction (100) where cutter (300) was rotated approximately 90 degrees.

FIGS. 1 and 2 are lateral perspectives of biocompatible construction (100). In FIG. 2, cutter 300 was rotated 90 degrees. With reference to FIGS. 1 and 2, biocompatible construction (100) is provided with anterior side (150), surgeon facing side (200), first lateral side (110), second lateral side (120) and rotatable cutter (300).

Anterior side (150) is provided with socket (180) and anterior cutting edge (152). Depending on preselected engineering parameters, socket (180) can extend through anterior side (150). In select preferred embodiments, anterior side (150) can be provided with one or more trapezoidal planes (154f, 154s, 156f, 156s).

Surgeon facing side (200) includes bearing (210) and first and second fittings (220f, 220s). First and second fittings (220f, 220s) are connectable to an insertion tool (not shown in FIGS. 1 and 2). Select embodiments of first and second fittings (220f, 220s) can include threads (222f, 222s).

Biocompatible construction (100) includes longitudinal axis X-X extending through socket (180) and bearing (210). Positioned between anterior side (150), surgeon facing side (200), first lateral side (110), second lateral side (120) are openings (130) lateral to longitudinal axis X-X.

In select preferred embodiments of biocompatible construction (100), lengths of first lateral side (110) and second lateral side (120) are greater than the widths of anterior side (150) and surgeon facing side (200). Such a configuration of biocompatible construction (100) causes longitudinal axis X-X to extend through socket (180) and bearing (210).

Figure 3:
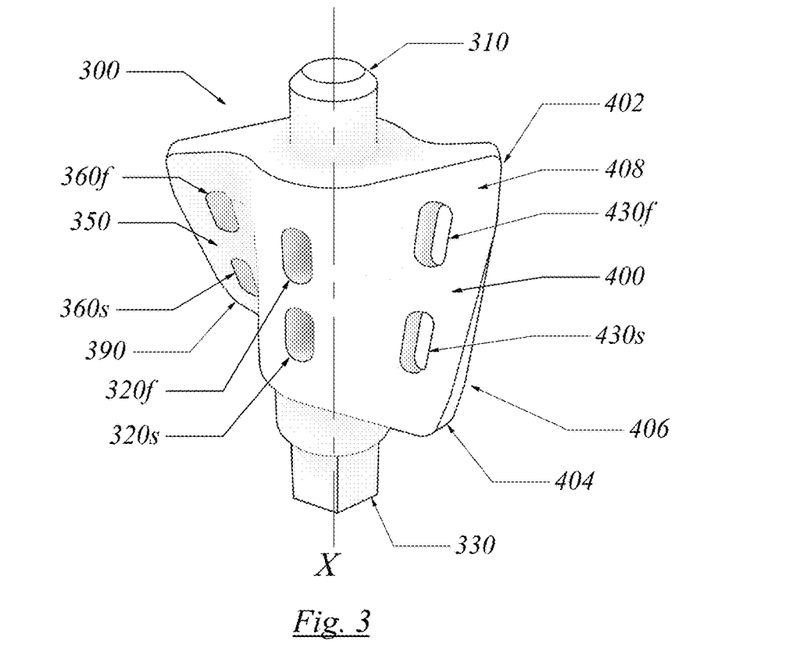
FIG. 3 is a first perspective of a preferred embodiment of rotatable cutter (300).
Figure 4:
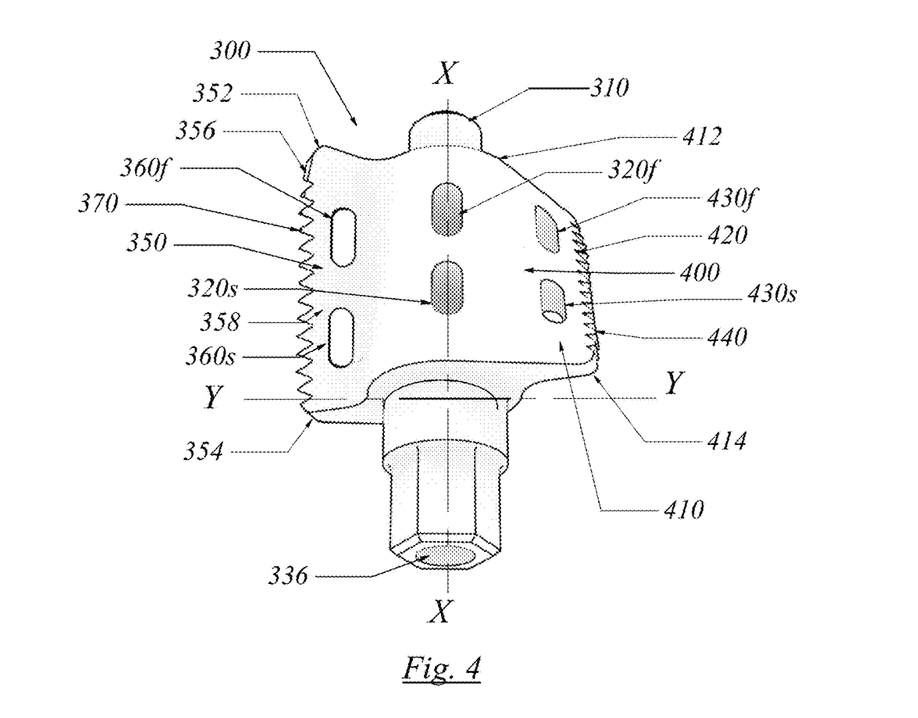
FIG. 4 is another perspective of a preferred embodiment of rotatable cutter (300).

FIGS. 3 and 4 are perspectives of rotatable cutter (300) of biocompatible construction (100). Rotatable cutter (300) is provided with stub axle (310), windows (320f, 320s), connector (330), first section (350) and second section (400). Preferred embodiments of first section (350) and second section (400) can include teeth (370, 440). In other select preferred embodiments, first section (350) is provided with one or more apertures (360f, 360s) and second section (400) is provided with one or more apertures (430f, 430s).

Regarding biocompatible construction (100) shown in FIGS. 1-6, stub axle (310) engages socket (180). According to predetermined engineering parameters, connector (330) can extend outward from bearing (210) toward the surgeon. In select preferred embodiments of the current invention, connector (330) can include a conduit (336) that, among other things, can provide a pathway for biocompatible medical devices and biocompatible osteogenic and/or other substances into or out of the interior volume of implantation into a created cavity. In select preferred embodiments of the current invention, stub axle (310) and connector (330) can surround longitudinal axis X-X. Connector (330) is connectable to a device (not shown) to rotate rotatable cutter (300).

Windows (320f, 320s) can be aligned with the longitudinal axis X-X, disposed between first section (350) and second section (400) and positioned between stub axle (310) and connector (330). For select preferred embodiments of rotatable cutter (300), stub axle (310), connector (330), first section (350) and second section (400) can be formed as an integral cutting unit.

First section (350) is disposed on a first side of longitudinal axis X-X and second section (400) is disposed on a second side of longitudinal axis X-X. For select preferred embodiments of rotatable cutter (300), first section (350) and second section (400) are opposed from each other in the same identical plane traverse to longitudinal axis X-X. Rotatable cutter (300) can include first section (350) extending from about anterior side (150) to about surgeon facing side (200) and second section (400) extending from about anterior side (150) to about surgeon facing side (200).

Figure 5:
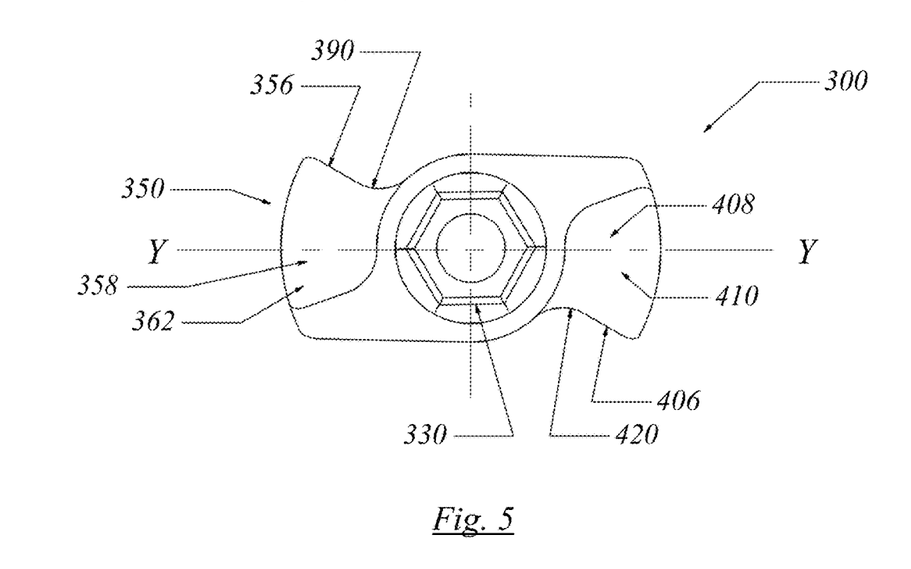
FIG. 5 is a cross-section of FIG. 3 along axis Y-Y that shows concave bends of first section (350) and second section (400) of rotatable cutter (300).

First section (350) includes a first lengthwise end (352) and an opposed second lengthwise end (354). First section (350) is also provided with a first blade (356) to cut a biological structure or tissue and a first noncutting edge (358) opposed to first blade (356). As best shown in FIG. 5, first blade (356) can be provided with a concave bend (390) relative to opposed first noncutting edge (358). In select preferred embodiments of biocompatible construction (100), first blade (356) is provided with serrations or teeth (370) or a combination thereof. In a first plane distinct from concave bend (390), first section (350) can include a first curvature (362) extending between the first lengthwise end (352) and the second lengthwise end (354). In select preferred embodiments of biocompatible construction (100), relative to longitudinal axis X-X, the first curvature (362) curves from a first point more proximate the longitudinal axis X-X toward a second point more distance from the longitudinal axis X-X. Among other things, it is believed that combination of concave bend (390) and first curvature (362) allows for graduated cutting of biological structures.

Second section (400) includes a first lengthwise end (402) and an opposed second lengthwise end (404). Second section (400) is also provided with a second blade (406) to cut a biological structure or tissue and a second noncutting edge (408) opposed to second blade (406). As best shown in FIG. 5, second blade (406) can be provided with a concave bend (420) relative to opposed second noncutting edge (408). In select preferred embodiments of biocompatible construction (100), second blade (406) is provided with teeth (440). In a first plane distinct from concave bend (420), second section (400) can include a first curvature (410) extending between the second lengthwise end (412) and the second lengthwise end (414). In select preferred embodiments of biocompatible construction (100), relative to longitudinal axis X-X, the first curvature (410) curves from a first point more proximate the longitudinal axis X-X toward a second point more distance from the longitudinal axis X-X. Among other things, it is believed that combination of concave bend (420) and first curvature (410) allows for graduated cutting of biological structures.

Figure 6:
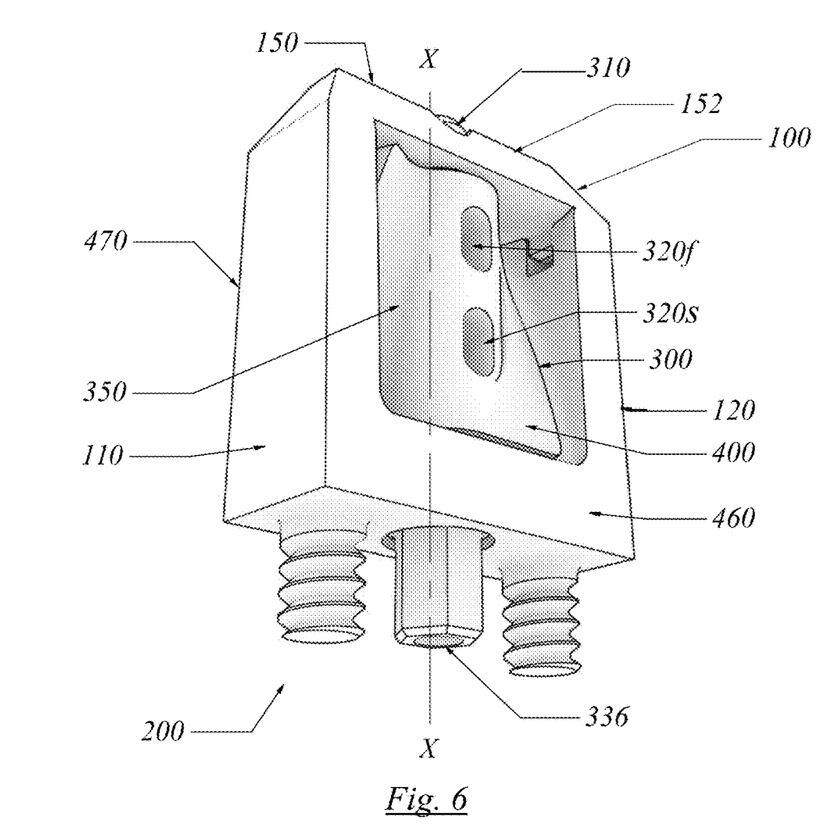
FIG. 6 is a perspective of a preferred embodiment of biocompatible construction (100) with trapezoidal first face (460) and trapezoidal second face (470).

As shown in FIG. 6, a preferred embodiment of biocompatible construction (100) can be provided with anterior side (150) where, in a first direction, anterior side (150) is of lessor length than surgeon facing side (200) such that the anterior side (150), surgeon facing side (200), first lateral side (110) and second lateral side (120) form a trapezoidal first face (460) and a trapezoidal second face (470).

Figure 7:
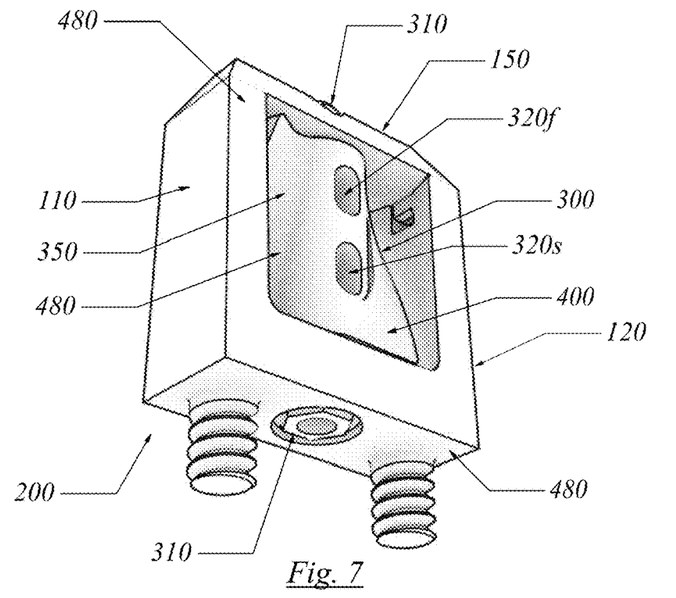
FIG. 7 is a perspective of a preferred embodiment of biocompatible construction (100) with surface treatments (480)

FIG. 7 is a perspective of a preferred embodiment of biocompatible construction (100) with surface treatments (480) such as micropores and/or barbs, etc. applied to anterior cutting edge (150), surgeon facing side (200), first lateral side (110), second lateral side (120) and rotatable cutter (300). It is believed that surface treatments (480) can assist with long term fixation of biocompatible construction (100) by allowing more bone ingrowth into biocompatible construction (100). Surface treatments (480) can be created by abrasive devices, chemical, laser, metal or abrasive particles incorporated into or onto the biocompatible composition or by other means acceptable in the art.

Figure 8:
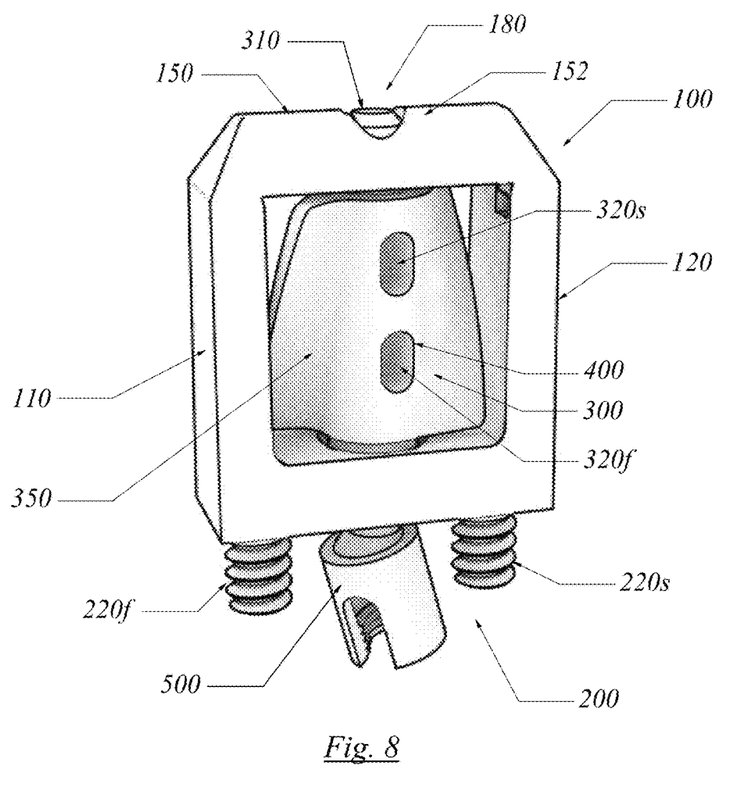
FIG. 8 is a perspective of biocompatible construction (100) provided with polyaxial adapter (500).

As shown in FIG. 8, biocompatible construction (100) is provided with polyaxial adapter (500) connectable to a device (not shown) distinct from biocompatible construction (100).

Figure 9:
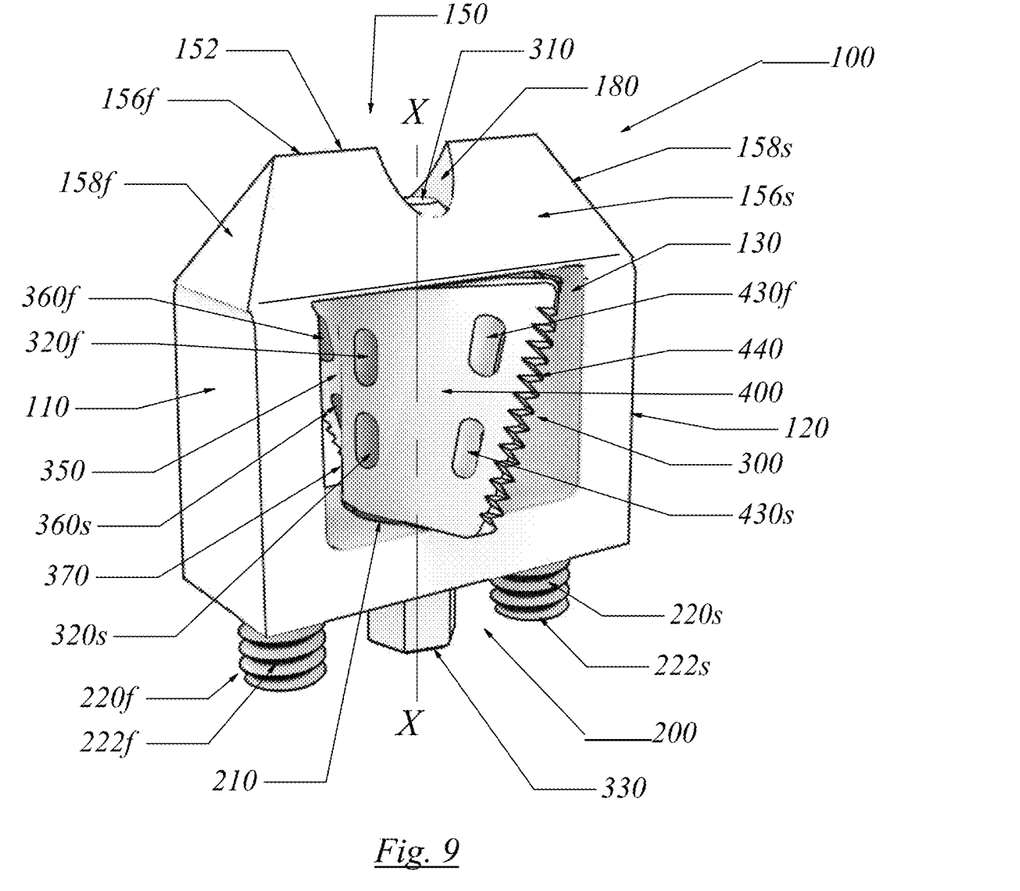
FIG. 9 is a perspective of rotatable cutter (300) and biocompatible construction (100).
Figure 10:
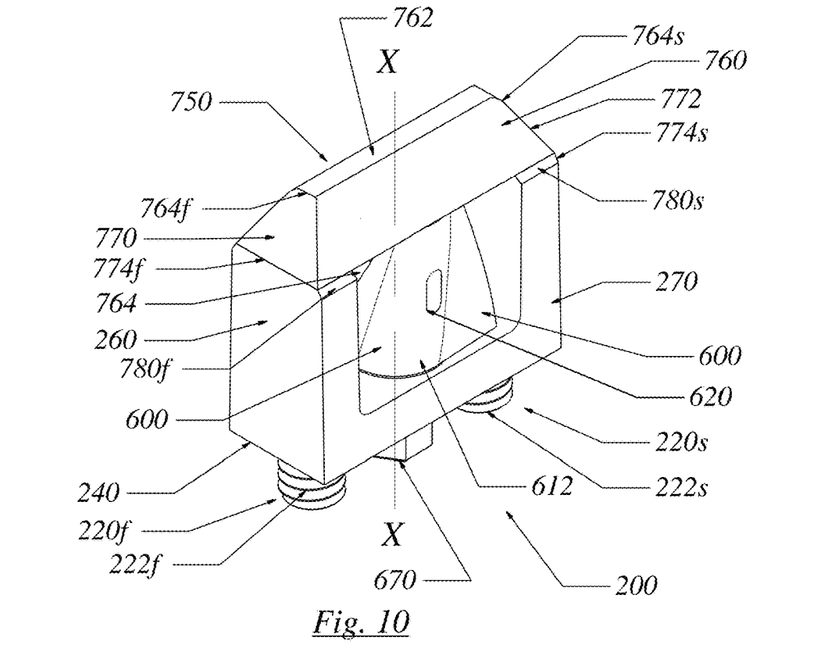
FIG. 10 is a first lateral perspective of a preferred embodiment of biocompatible construction (100).
Figure 11:
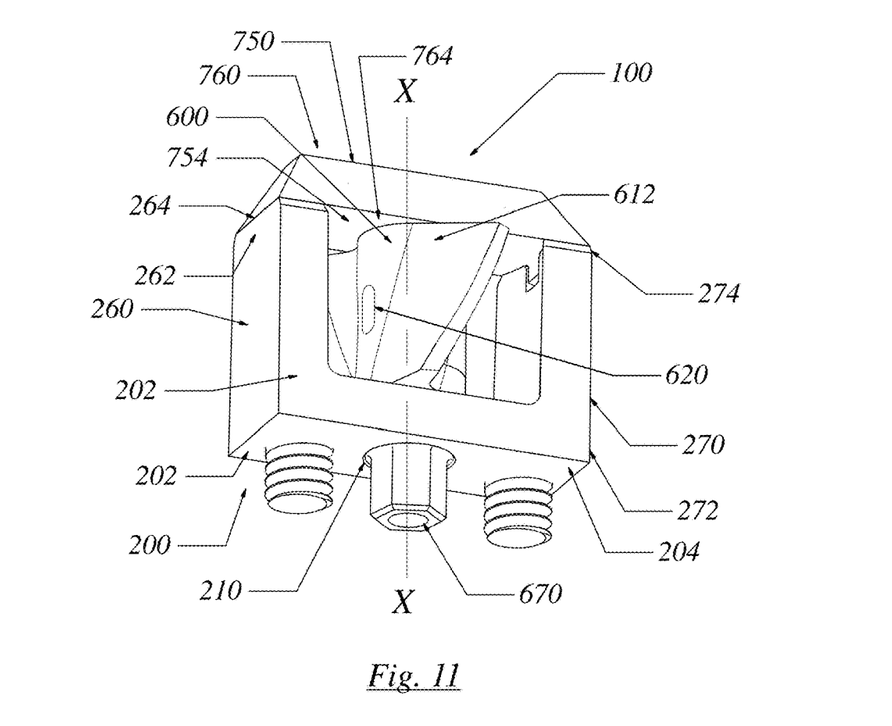
FIG. 11 is a second lateral perspective of the FIG. 1 preferred embodiment of biocompatible construction (100) where cutter (600) was rotated approximately 90 degrees.

FIG. 9 is a perspective of rotatable cutter (300) and biocompatible construction (100). Along with rotatable cutter (300), biocompatible construction (100) is provided with anterior side (150), surgeon facing side (200), first lateral side (110) and second lateral side (120).

Anterior side (150) is provided with socket (180) and anterior cutting edge (152). Depending on preselected engineering parameters, socket (180) can extend through anterior side (150). In select preferred embodiments, anterior side (150) can be provided with one or more trapezoidal planes (156f, 156s) and one or more triangular planes (158f, 158s).

Surgeon facing side (200) includes bearing (210) and first and second fittings (220f, 220s). First and second fittings (220f, 220s) are connectable to an insertion tool (not shown in FIGS. 1 and 2). Select embodiments of first and second fittings (220f, 220s) can include threads (222f, 222s).

Rotatable cutter (300) is provided with stub axle (310), windows (320f, 320s), connector (330), first section (350) and second section (400). Preferred embodiments of first section (350) and second section (400) can include teeth (370, 440). In other select preferred embodiments, first section (350) is provided with one or more apertures (360f, 360s) and second section (400) is provided with one or more apertures (430f, 430s).

Regarding biocompatible construction (100) shown in FIG. 9, stub axle (310) engages socket (180). According to predetermined engineering parameters, connector (330) can extend outward from bearing (210) toward the surgeon. In select preferred embodiments of the current invention, connector (330) can include a conduit (336) (not shown in FIG. 9) that, among other things, can provide a pathway for biocompatible medical devices and biocompatible osteogenic and/or other substances into or out of the interior volume of implantation into a created cavity. In select preferred embodiments of the current invention, stub axle (310) and connector (330) can surround longitudinal axis X-X. Connector (330) is connectable to a device (not shown) to rotate rotatable cutter (300).

Windows (320f, 320s) can be aligned with the longitudinal axis X-X, disposed between first section (350) and second section (400) and positioned between stub axle (310) and connector (330). For select preferred embodiments of rotatable cutter (300), stub axle (310), connector (330), first section (350) and second section (400) can be formed as an integral cutting unit.

First section (350) is disposed on a first side of longitudinal axis X-X and second section (400) is disposed on a second side of longitudinal axis X-X. For select preferred embodiments of rotatable cutter (300), first section (350) and second section (400) are opposed from each other. Rotatable cutter (300) can include first section (350) extending from about anterior side (150) to about surgeon facing side (200) and second section (400) extending from about anterior side (150) to about surgeon facing side (200).

With the exception of teeth (370, 440) shown in some of the Drawings, first section (350) and second section (400) portrayed in FIG. 9 are identical to the previously disclosed first sections (350) and (400).

As measured along longitudinal axis X-X of biocompatible construction (100), preferred embodiments are provided with anterior cutting edge (152) that can be up to about 30 millimeters in length. The length of biocompatible construction (100), including anterior cutting edge (152) can be from about 6 millimeters to about 50 millimeters. Cross-sectional widths of anterior side (150) can range from about 12 millimeters$^2$ to about 200 millimeters$^2$. Cross-sectional widths of biocompatible construction (100), other than anterior side (150) can range from about 16 millimeters$^2$ to about 320 millimeters$^2$.

With reference to FIGS. 10-17, a preferred embodiment of biocompatible construction (100) is enabled. Biocompatible construction (100) includes frame (240), rotatable integral or single-piece cutter (600), complimentary anterior plate (750), one or more welds (780f, 780s) and lock (792).

Frame (240) of biocompatible construction (100) includes surgeon facing side (200). Surgeon facing side (200) is provided with bearing (210) extending through surgeon facing side (200). First side (262) of first lateral support (260) is connected to first side (202) of surgeon facing side (200). First lateral support (260) is also provided with second side (264) opposite from the surgeon facing side (200). First side (272) of second lateral support (270) is connected to second side (204) of surgeon facing side (200). Second lateral support (270) is also provided with second side (274) of the second lateral support (270) opposite from the surgeon facing side (200).

Figure 12:
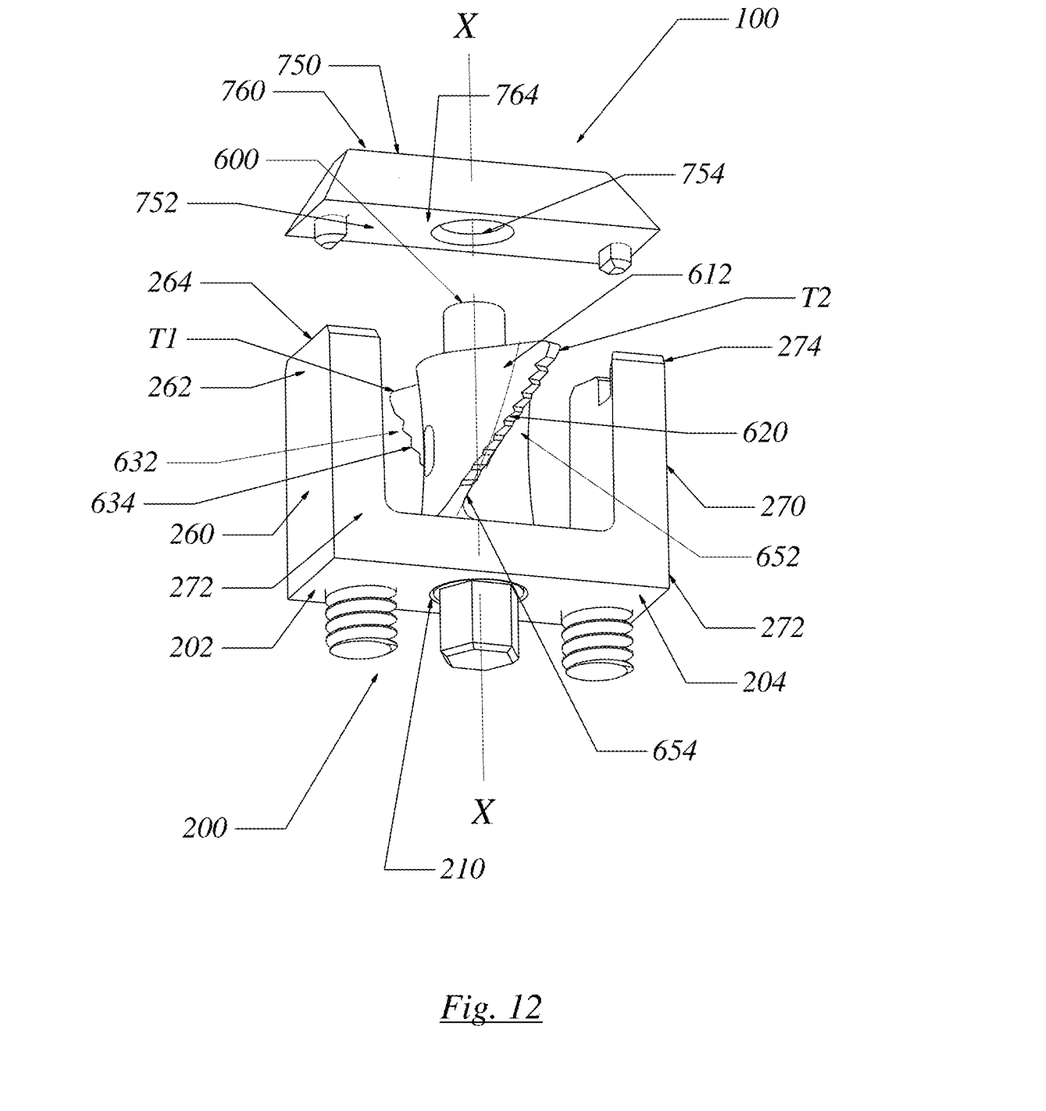
FIG. 12 is an exploded perspective of a preferred embodiment of biocompatible construction (100).
Figure 17:
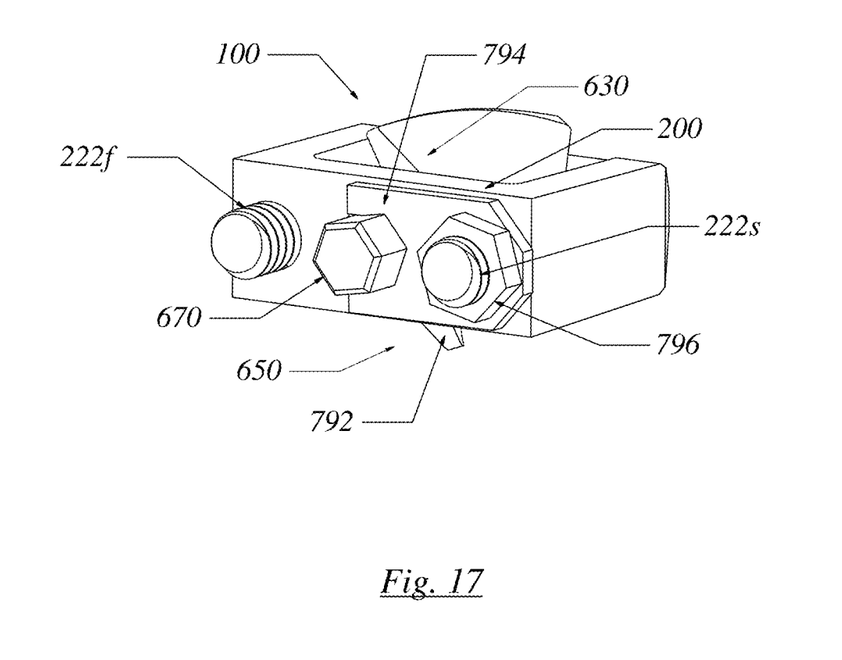
FIG. 17 is perspective of surgeon facing side (200) of biocompatible construction (100).

In select preferred embodiments, frame (240) is a single piece that includes integral surgeon facing side (200), first lateral side or bend (260) and second lateral side or bend (270). Surgeon facing side (200) can be provided with first and second fittings (220f, 220s) that are connectable to an insertion device distinct from biocompatible construction (100).

Figure 13:
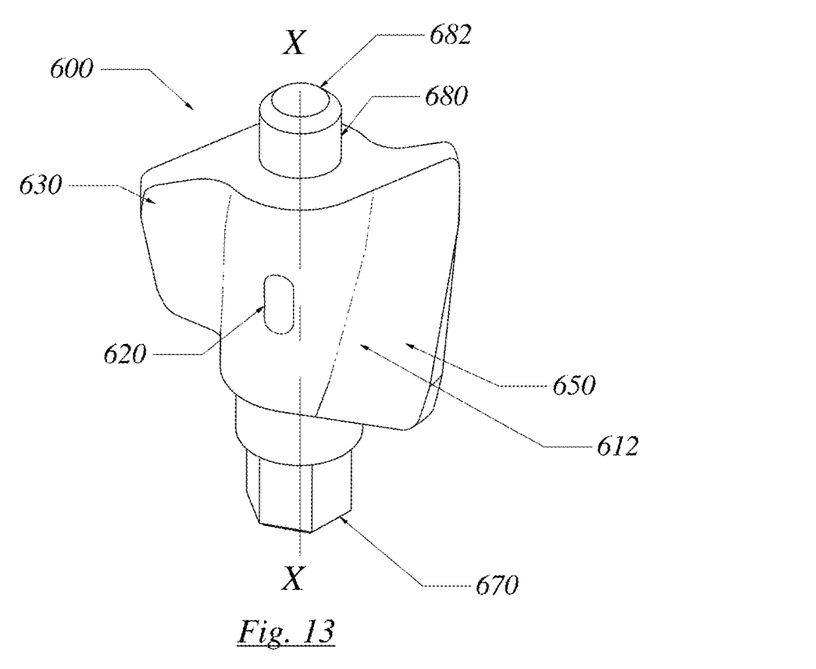
FIG. 13 is a perspective of a preferred embodiment of rotatable cutter (600).
Figure 14:
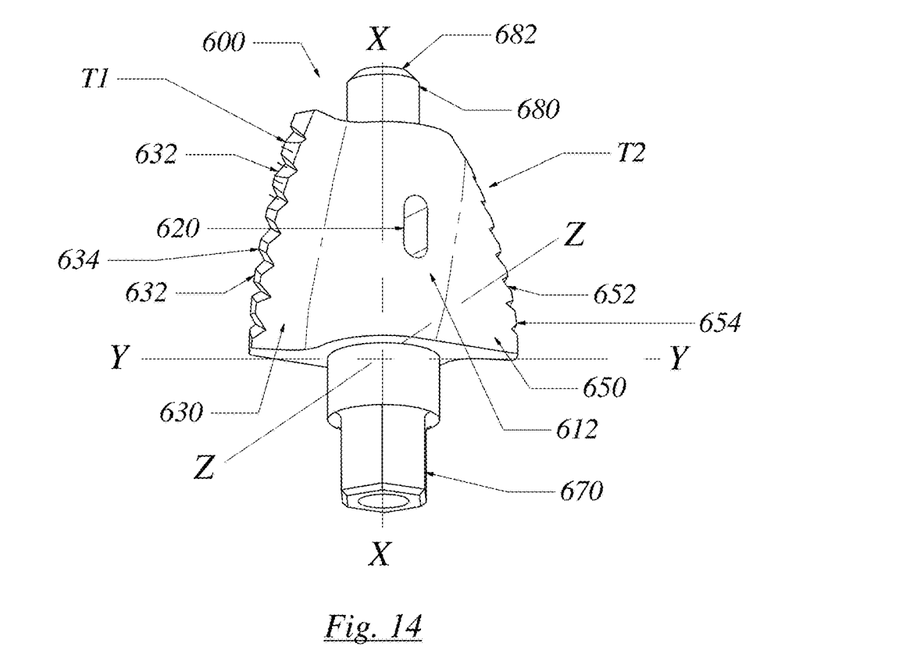
FIG. 14 is a perspective of a preferred embodiment of rotatable cutter (600).
Figure 16:
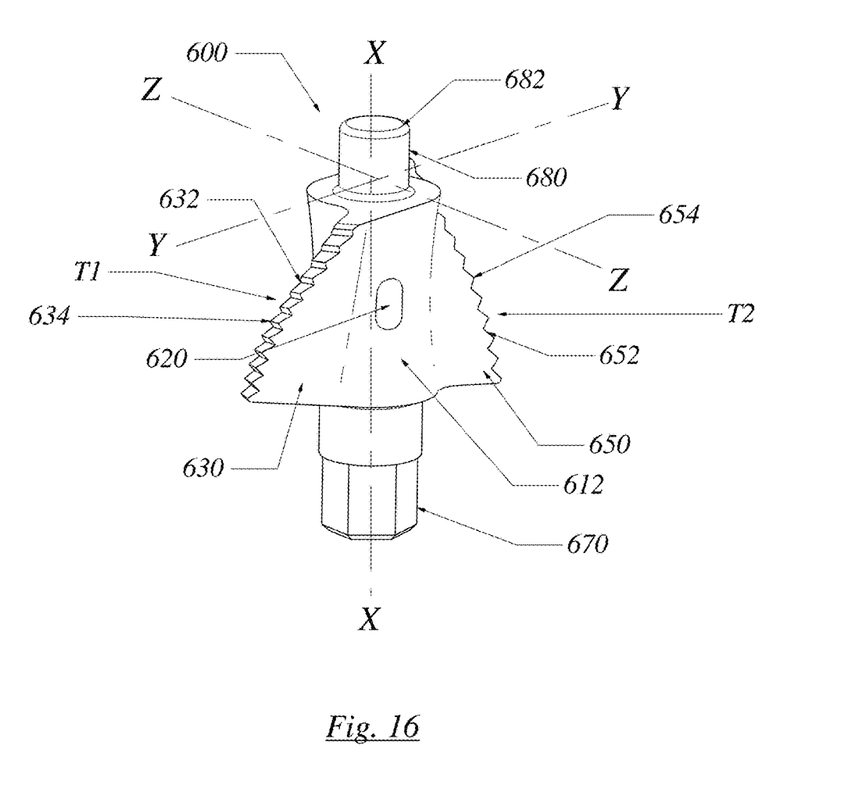
FIG. 16 is a perspective of a preferred embodiment of rotatable cutter (600).

Within the scope of the current invention, rotatable integral or single-piece cutter (600) of biocompatible construction (100) is adapted to generate a local autograft of subchondral bone at the joint or surgically created cavity. Rotatable integral cutter (600) includes central body (612) that has a longitudinal axis (X-X), a height axis (Y-Y) and a depth axis (Z-Z) that extend through rotatable integral cutter (600). In select preferred embodiments, central body (612) is provided with centralized aperture (620) that is adapted to enhance dispersal of the generated autograft about the joint or surgically created cavity. Depending on surgical parameters, osteogenic and/or other substances, distinct from the patient, can be loaded into centralized aperture (620).

Figure 15:
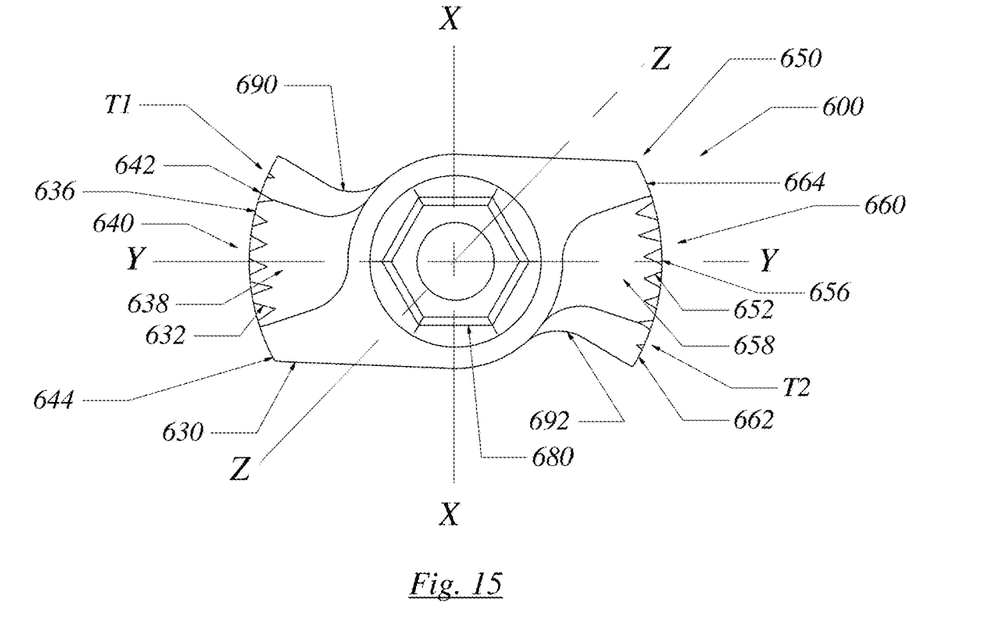
FIG. 15 is a cross-section of FIG. 14 that shows concave bends of first section (630) and second section (650) of rotatable cutter (600).

In select preferred embodiments of biocompatible composition (100), first teeth (632) can be positioned on first cutting blade (636) of rotatable integral cutter (600). First noncutting edge (638) is opposed from first cutting blade (636). Cutting blade (636) can include a concave bend (690) relative to opposed first noncutting edge (638). First flared section (630) can include first curvature (640) between first lengthwise end (642) opposed second lengthwise end (644) of first noncutting edge (638). Relative to the longitudinal axis (X-X), first curvature (640) curves from a first point more proximate to the longitudinal axis (X-X) to a second point more distant from the longitudinal axis (X-X).

First flared section (630) is positioned on a first side of central body (612) and extends away from the longitudinal axis (X-X). Among other things, first flared section (630) is provided with first teeth (632) positioned on a first peripheral edge (634) of first cutting blade (636) of first flared section (630). First peripheral edge (634) includes track 1 (T1) that engages and curves through the longitudinal axis (X-X), the height axis (Y-Y) and depth axis (Z-Z) of rotatable integral cutter (600). Relative to the longitudinal axis (X-X), the height axis (Y-Y) and depth axis (Z-Z) of rotatable integral cutter (600), locations of at least some of the first teeth (632) are three dimensionally diverse from other first teeth (632). The lengthwise track 1 (T1) of peripheral edge (634) causes some of the first teeth (632) to be positioned in at least one of the three axes (X-X, Y-Y, Z-Z) distinct from the positions and locations of other first teeth (632).

In select preferred embodiments of biocompatible composition (100), second teeth (652) can be positioned on second cutting blade (656) of rotatable integral cutter (600). Second noncutting edge (658) is opposed from the second blade (656). Second cutting blade (658) can include comprises concave bend (692) relative to the second noncutting edge (658). Second flared section (650) can include second curvature (660) between a first lengthwise end (662) and an opposed second lengthwise end (664) of the second noncutting edge (658). Relative to the longitudinal axis (X-X), second curvature (660) curves from a first point more proximate to the longitudinal axis (X-X) to a second point more distant from the longitudinal axis (X-X).

Second flared section (650) is positioned on a second side of central body (612) and extends away from the longitudinal axis (X-X). Among other things, second flared section (650) is provided with second teeth (652) positioned on a second peripheral edge (654) of second cutting blade (658) of second flared section (650). Second peripheral edge (654) includes track 2 (T2) that engages and curves through the longitudinal axis (X-X), the height axis (Y-Y) and depth axis (Z-Z) of rotatable integral cutter (600). Relative to the longitudinal axis (X-X), the height axis (Y-Y) and depth axis (Z-Z) of rotatable integral cutter (600), locations of at least some of the second teeth (652) are three dimensionally diverse from other second teeth (652). The lengthwise track 2 (T2) of second peripheral edge (654) causes some of the second teeth (652) to be positioned in at least one of the three axes (X-X, Y-Y, Z-Z) distinct from the positions and locations of other second teeth (652).

When rotatable integral cutter (600) is rotated, first and second teeth (632, 652) can generate an autograft having particle sizes in the range of from about 50 cubic millimeters to about 6 cubic millimeters or less. Within the scope of the current biocompatible construction (100), it is anticipated that approximately ninety percent of the generated autograph particles will 6 cubic millimeters or less. The generated particles are localized at the joint or surgically created cavity.

First stub axle (670) extends away from central body (612) along longitudinal axis (X-X) and into the bearing (210). Second stub axle (680) extends away from central body (612) along the longitudinal axis (X-X) in a direction opposite from bearing (210) of surgeon facing side (200). In select preferred embodiments, first stub axle (670) can extend into and through bearing (210).

Anterior plate (750) of biocompatible construction (100) is adapted to distract and to cut tissue or bone with application of forward force. In preferred embodiments of biocompatible construction (100), anterior plate (750) is distinct from frame (240) and rotatable cutter (600).

Interior side (752) of anterior plate (750) can be provided with receptacle (754) adapted to engage nose (682) of second stub axle (680). Select preferred embodiments of anterior plate (750) include uninterrupted exterior face (760) with anterior cutting edge (762) where anterior cutting edge (762) of uninterrupted exterior face (760) is of lesser length than interior side (752) of uninterrupted exterior face (760). Anterior plate (750) can also include first blunted zone (770) and second blunted zone (772) that extend between opposed ends (764f, 764s) of the anterior cutting edge (762) and external margins (774f, 774s) of the interior side (752).

One or more welds (780f, 780s) can secure anterior plate (750) to nose (682) of second stub axle (680), second side (264) of first lateral support (260) and second side (274) of the second lateral support (270).

Lock (792) is adapted to secure the first flared section (630) and the second flared section (650) in a direction aligned with the height axis (Y-Y) of the integral rotatable cutter (600). In select preferred embodiments, lock (792) can include clip (794) and locking nut (796). Locking nut (796) locks clip (794) about either fitting (222f) or fitting (222s) of biocompatible construction (100). Lock clip (794) can prevent second stub axle (670) from rotating such that first flared section (630) and the second flared section (650) are aligned in a direction with the height axis (Y-Y) of the integral rotatable cutter (600).

Select preferred embodiments of the current invention have been disclosed and enabled as required by Title 35 of the United States Code and/or the Articles of the Patent Cooperation Treaty.

What is claimed is:

1. A biocompatible construction for implantation into a joint or surgically created cavity; the biocompatible construction comprising:
   a) a frame comprising:
      i) a surgeon facing side comprising a bearing;
      ii) a first side of a first lateral support connected to a first side of the surgeon facing side and a second side of the first lateral support opposite from the surgeon facing side; and
      iii) a first side of a second lateral support connected to a second side of the surgeon facing side, opposite from the first side of the first lateral support, and a second side of the second lateral support opposite from the surgeon facing side;
   b) a rotatable integral cutter adapted to generate an autograft of articular cartilage and subchondral bone at the joint or surgically created cavity; the rotatable integral cutter further comprising:
      i) a central body comprising;
         a longitudinal axis (X-X), a height axis (Y-Y) and a depth axis (Z-Z) extending through the rotatable integral cutter;
         a centralized aperture adapted to enhance dispersal of the generated autograft about the joint or surgically created cavity;
         a first flared section, positioned on a first side of the central body, extending away from the longitudinal axis (X-X); the first flared section comprising first teeth, wherein relative to the longitudinal axis (X-X), the height axis (Y-Y) and depth axis (Z-Z) of the rotatable integral cutter, locations of at least some of the first teeth are three dimensionally diverse from other first teeth;
         a second flared section, positioned on a second side of the central body, extending away from the longitudinal axis (X-X); the second flared section comprising second teeth, wherein relative to the longitudinal axis (X-X), the height axis (Y-Y) and depth axis (Z-Z) of the rotatable integral cutter, locations of at least some of the second teeth are three dimensionally diverse from other second teeth, and wherein first and second teeth generate the autograft having particle sizes in the range of from about 50 cubic millimeters to about 6 cubic millimeters or less;
      ii) a first stub axle extending away from the central body, along the longitudinal axis (X-X) and into the bearing;
      iii) a second stub axle extending away from the central body, along the longitudinal axis (X-X), in a direction opposite the bearing;
   c) an anterior plate, attached to the frame, adapted to distract and to cut with application of forward force; the anterior plate comprising:
      i) an interior side comprising a receptacle adapted to engage a nose of the second stub axle;
      ii) an uninterrupted exterior face comprising an anterior cutting edge, wherein the anterior cutting edge of uninterrupted exterior face is of lesser length than the interior side of uninterrupted exterior face; and
      iii) first and second blunted zones extending between opposed ends of the anterior cutting edge and external margins of the interior side;
   d) one or more welds securing the anterior plate to the nose of the second stub axle, the second side of the first lateral support and the second side of the second lateral support; and
   e) a lock adapted to secure the first flared section and the second flared section in a direction aligned with the height axis (X-X) of the integral rotatable cutter.

2. The biocompatible construction of claim 1, wherein:
   a) the first flared section comprises:
      i) the first teeth positioned on a first cutting blade; and
      ii) a first noncutting edge opposed from the first cutting blade, wherein the first cutting blade comprises a concave bend relative to the opposed first noncutting edge; and
   b) the second flared section comprises:
      i) the second teeth positioned on a second cutting blade; and
      ii) a second noncutting edge opposed from the second blade, wherein the second blade comprises a concave bend relative to the second noncutting edge.

3. The biocompatible construction of claim 2, wherein:
   a) the first flared section comprises a first curvature between a first lengthwise end and an opposed second lengthwise end of the first noncutting edge, wherein, relative to the longitudinal axis (X-X), the first curvature curves from a first point more proximate to the longitudinal axis (X-X) to a second point more distant from the longitudinal axis (X-X); and
   b) the second flared section comprises a second curvature between a first lengthwise end and an opposed second lengthwise end of the second noncutting edge, wherein, relative to the longitudinal axis (X-X), the second curvature curves from a first point more proximate to the longitudinal axis (X-X) to a second point more distant from the longitudinal axis (X-X).

4. The biocompatible construction of claim 3, wherein the surgeon facing side comprises first and second fittings connectable to an insertion device distinct from the biocompatible construction.

5. The biocompatible construction of claim 4, wherein the first stub axle extends into and through the bearing.

6. A biocompatible construction for implantation into a joint or surgically created cavity; the biocompatible construction comprising:
   a) an integral frame comprising:
      i) a surgeon facing side comprising a bearing;
      ii) a first lateral bend extending away from a plane of the surgeon facing side;
      iii) a second lateral bend extending away from the plane of the surgeon facing side;
   b) a rotatable integral cutter adapted to generate an autograft of articular cartilage and subchondral bone at the joint or surgically created cavity; the rotatable integral cutter further comprising:
      i) a central body comprising;
         a longitudinal axis (X-X), a height axis (Y-Y) and a depth axis (Z-Z) extending through the rotatable integral cutter;
         a centralized aperture adapted to enhance dispersal of the generated autograft about the joint or surgically created cavity;
         a first flared section, positioned on a first side of the central body, extending away from the longitudinal axis (X-X); the first flared section comprising first teeth, wherein relative to the longitudinal axis (X-X), the height axis (Y-Y) and depth axis (Z-Z) of the rotatable integral cutter, locations of at least some of the first teeth are three dimensionally diverse from other first teeth;

a second flared section, positioned on a second side of the central body, extending away from the longitudinal axis (X-X); the second flared section comprising second teeth, wherein relative to the longitudinal axis (X-X), the height axis (Y-Y) and depth axis (Z-Z) of the rotatable integral cutter, locations of at least some of the second teeth are three dimensionally diverse from other second teeth, and wherein first and second teeth generate the autograft having particle sizes in the range of from about 50 cubic millimeters to about 6 cubic millimeters or less;

ii) a first stub axle extending away from the central body, along the longitudinal axis (X-X) and into the bearing;

iii) a second stub axle extending away from the central body, along the longitudinal axis (X-X), in a direction opposite the bearing;

c) an anterior plate adapted to distract and to cut with application of forward force; the anterior plate comprising:
  i) an interior side comprising a receptacle adapted to engage a nose of the second stub axle; and
  ii) an uninterrupted exterior face comprising an anterior cutting edge, wherein the anterior cutting edge of uninterrupted exterior face is of lesser length than the interior side of uninterrupted exterior face; and d) one or more welds securing the anterior plate to the nose of the second stub axle, the first lateral bend and the second lateral bend.

7. The biocompatible construction of claim 6, wherein:
a) the first flared section comprises:
  i) the first teeth positioned on a first cutting blade; and
  ii) a first noncutting edge opposed from the first cutting blade, wherein the first cutting blade comprises a concave bend relative to the opposed first noncutting edge; and
b) the second flared section comprises:
  i) the second teeth positioned on a second cutting blade; and
  ii) a second noncutting edge opposed from the second blade, wherein the second blade comprises a concave bend relative to the second noncutting edge.

8. The biocompatible construction of claim 7 comprising a lock adapted to secure the first flared section and the second flared section in a direction aligned with the height axis (Y-Y) of the rotatable integral cutter.

9. The biocompatible construction of claim 8, wherein:
a) the first flared section comprises a first curvature between a first lengthwise end and an opposed second lengthwise end of the first noncutting edge, wherein, relative to the longitudinal axis (X-X), the first curvature curves from a first point more proximate to the longitudinal axis (X-X) to a second point more distant from the longitudinal axis (X-X); and
b) the second flared section comprises a second curvature between a first lengthwise end and an opposed second lengthwise end of the second noncutting edge, wherein, relative to the longitudinal axis (X-X), the second curvature curves from a first point more proximate to the longitudinal axis (X-X) to a second point more distant from the longitudinal axis (X-X).

10. The biocompatible construction of claim 9 comprising a first blunted zone and a second blunted zone; the blunted zones extending between opposed ends of the anterior cutting edge and external margins of the interior side.

11. The biocompatible construction of claim 10, wherein the surgeon facing side (200) comprises first and second fittings connectable to an insertion device distinct from the biocompatible construction.

12. The biocompatible construction of claim 11, wherein the first stub axle extends into and through the bearing.

13. A biocompatible construction for implantation into a joint or surgically created cavity; the biocompatible construction comprising:
a) a single-piece frame comprising:
  i) a surgeon facing side comprising a bearing;
  ii) a first lateral bend extending away from a plane of the surgeon facing side;
  iii) a second lateral bend extending away from the plane of the surgeon facing side;
b) a complimentary anterior plate adapted to distract and to cut with application of forward force; the complimentary anterior plate connected to:
  i) an exposed end of first lateral bend of the single-piece frame;
  ii) an exposed end of second lateral bend of the single-piece frame; and
c) a rotatable single-piece cutter having a longitudinal axis (X-X), a height axis (Y-Y) and a depth axis (Z-Z); the rotatable single-piece cutter connected to the bearing and the inward side of the anterior plate; the rotatable single-piece cutter comprising: a first plurality of first teeth positioned outward from the longitudinal axis (X-X) and a second plurality of second teeth positioned outward from the longitudinal axis (X-X); the first plurality of first teeth and the second plurality of second teeth adapted to generate an autograft having particle sizes in the range of from about 50 cubic millimeters to about 6 cubic millimeters or less.

14. The biocompatible construction of claim 13, wherein the rotatable single-piece cutter comprises:
a) a centralized aperture positioned on a central body of the rotatable cutter; the centralized aperture adapted to enhance dispersal of the generated autograft about the joint or surgically created cavity;
b) a first stub axle connecting the rotatable single-piece cutter to bearing;
c) a second stub axle connecting the rotatable single-piece cutter to a receptacle of inward side of the anterior plate;
d) a first flared section, positioned on a first side of the central body, the first flared section carrying the first plurality of first teeth, wherein relative to the longitudinal axis (X-X), the height axis (Y-Y) and depth axis (Z-Z) of the rotatable integral cutter, locations of at least some of the first teeth are three dimensionally diverse from other first teeth; and
e) a second flared section, positioned on a second side of the central body, the second flared section carrying the second plurality of second teeth, wherein relative to the longitudinal axis (X-X), the height axis (Y-Y) and depth axis (Z-Z) of the single-piece cutter, locations of at least some of the second teeth are three dimensionally diverse from other second teeth.

15. The biocompatible construction of claim 14, wherein an exterior face comprises an anterior cutting edge, wherein the anterior cutting edge of exterior face is of lesser length than the interior side of uninterrupted exterior face.

16. The biocompatible construction of claim 15 comprising a lock adapted to secure the first flared section and the second flared section in alignment with the height axis (Y-Y) of the rotatable single-piece cutter.

17. The biocompatible construction of claim 16, wherein:
a) the first flared section comprises a first curvature between a first lengthwise end and an opposed second lengthwise end of a first noncutting edge, wherein, relative to the longitudinal axis (X-X), the first curvature curves from a first point more proximate to the longitudinal axis (X-X) to a second point more distant from the longitudinal axis (X-X); and
b) the second flared section comprises a second curvature between a first lengthwise end and an opposed second lengthwise end of a second noncutting edge, wherein, relative to the longitudinal axis (X-X), the second curvature curves from a first point more proximate to the longitudinal axis (X-X) to a second point more distant from the longitudinal axis (X-X).

18. The biocompatible construction of claim 17 comprising a first blunted zone and a second blunted zone; the blunted zones extending between opposed ends of the anterior cutting edge and external margins of the interior side.

19. The biocompatible construction of claim 18, wherein the surgeon facing side comprises first and second fittings connectable to an insertion device distinct from the biocompatible construction.

20. The biocompatible construction of claim 19, wherein the first stub axle extends into and through the bearing.

* * * * *